United States Patent [19]

Bailey

[11] Patent Number: 4,461,075
[45] Date of Patent: Jul. 24, 1984

[54] METHOD OF MAKING A STIMULATING ELECTRODE

[75] Inventor: William D. Bailey, Wayzata, Minn.

[73] Assignee: Stimtech, Inc., Minneapolis, Minn.

[21] Appl. No.: 393,918

[22] Filed: Jun. 30, 1982

Related U.S. Application Data

[62] Division of Ser. No. 8,011, Jan. 31, 1979, Pat. No. 4,367,755.

[51] Int. Cl.³ .............................................. H01R 43/00
[52] U.S. Cl. ...................................................... 29/825
[58] Field of Search ......................... 29/825, 883, 889; 128/641, 642

[56] References Cited

U.S. PATENT DOCUMENTS

| | | | |
|---|---|---|---|
| 3,295,515 | 1/1967 | Kahn | 128/640 |
| 4,008,300 | 2/1977 | Ponn | 29/825 X |
| 4,011,861 | 3/1977 | Enger | 128/642 |
| 4,051,842 | 10/1977 | Hazel et al. | 128/640 |
| 4,063,352 | 12/1977 | Bevilacqua | 29/884 |
| 4,079,731 | 3/1978 | Danby | 128/641 |

*Primary Examiner*—Howard N. Goldberg
*Assistant Examiner*—Carl J. Arbes

[57] ABSTRACT

An electrode for tissue stimulating applications, such as pain control, includes a conductive flexible pad such as polymer gel, or karaya gum, interfacing with the patient. A backing layer is composed of conductive silicone rubber, has a multiplicity of perforations therethrough, and defines an integral protuberance for connection with external apparatus.

2 Claims, 4 Drawing Figures

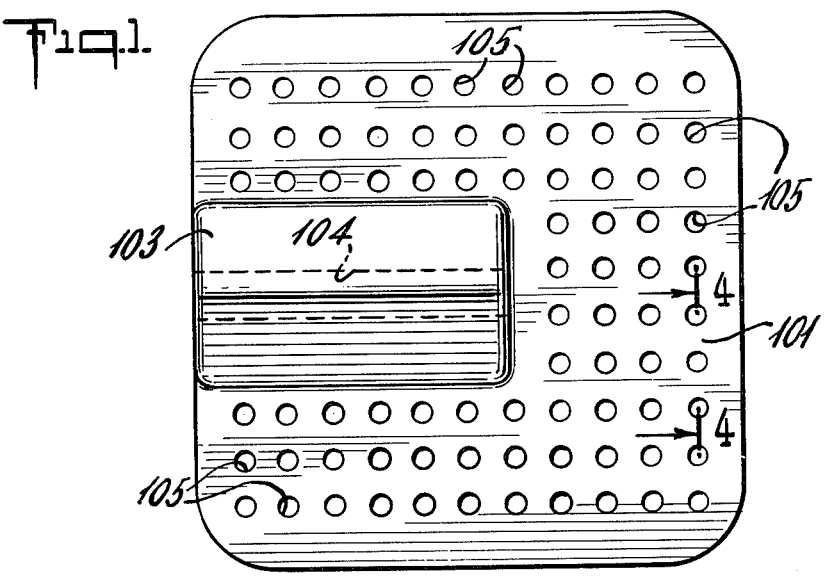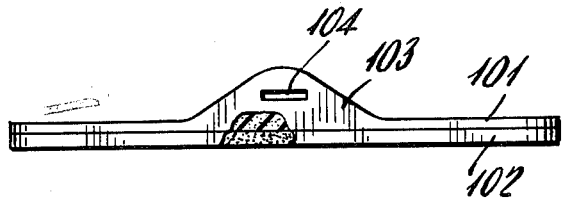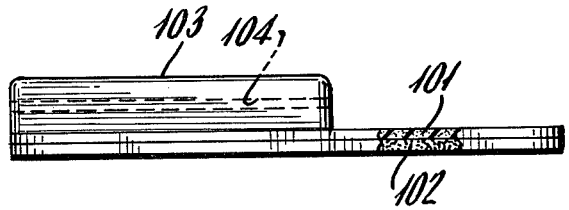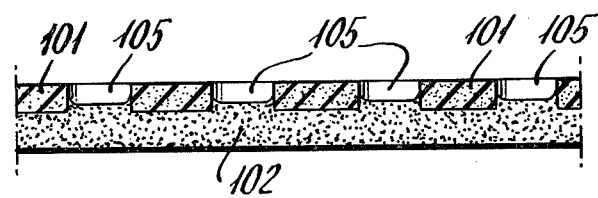

METHOD OF MAKING A STIMULATING ELECTRODE

This is a division of application Ser. No. 8,011, filed Jan. 31, 1979 now U.S. Pat. No. 4,367,755 issued Jan. 11, 1983.

FIELD OF THE INVENTION

This invention relates to stimulating electrodes, and more particularly to electrodes which find application in the field of transcutaneous electical nerve stimulation, such as for pain control.

BACKGROUND AND PRIOR ART

Electronic pain control has provided an effective and widely successful mode of patient treatment, particularly for chronic and post-operative pain conditions. While the circuitry and signalling aspects of electronic pain control are reasonably refined, electrode design and construction continues to be an area ripe for development and improvement. Hence, while it is generally understood that factors of patient comfort, electrode flexibility, electrode adhesive and removability characteristics, uniformity of electrical current density, and the like parameters are desirable design goals, most designs involve compromises or tradeoffs between the respective factors, with most electrodes involving relative strengths in some aspects but consequent disadvantages in others.

It is a principal object of the present invention to provide electrodes for electronic pain control applications, which have superior overall performance characteristics.

One class of electrode is exemplified in U.S. Pat. No. 4,066,078 to Berg, setting forth an electrode having an electrically conductive polymer adhesive gel, and a suitable non-conductive backing, whereby the gel is directly coupled to the skin of the patient. Another type of electrode is exemplified by U.S. Pat. No. 4,125,110 to Hymes, utilizing karaya gum as the electrically conductive patient interface, suitably backed by non-conductive material.

Many of the known electrodes either of the type exemplified by the Berg patent, or of the type exemplified by the Hymes patent, exhibit the lack of ability to "breathe", that is, the ability to be able to dissipate absorbed moisture which is absorbed from the skin. Often, if electrodes do not have this "breathing" ability, actual physical swelling of the electrode occurs, with consequent uncertainty as to the physical dimensions and correspondingly the electrical characteristics of the material as an electrode.

It is accordingly an object of the present invention to provide electronic pain control electrodes wherein absorbed moisture, obtained either from the skin of the patient or from the ambient atmosphere, is effectively dissipated while dimensional and electrical stability is maintained.

Another difficulty often associated with electrodes of the types aforementioned is mechanical adhesion of the gelatinous pad to the non-conductive backing. During removal or adjustment of the electrode relative to the skin, the pad experiences tension and shear forces caused by the lifting of the backing material, which forces are distributed to the skin-pad and the pad-backing interfaces.

It is accordingly an object of the present invention to provide electrodes which, while functionally superior from the standpoint of comfort, adhesionability, and moisture dissipation characteristics, are furthermore possessed of superior structural strength whereby tension and shear forces encountered in removal or the like operations, have minimal effect in altering the physical and electrical characteristics of the electrode.

SUMMARY OF THE INVENTION

In accordance with the principles of the present invention, a stimulating electrode is defined by an electrically conductive flexible pad, such as of conductive polymer adhesive gel or karaya gum base materials, to which there is attached a backing layer composed of conductive silicone rubber. The conductive rubber pad is provided with a multiplicity of perforations therein, whereby the gel pad is permitted to dissipate moisture taken on from the skin, and further whereby the backing-pad interface is provided with considerabe structural strength relative to tensile and shear forces occasioned by electrode movement or removal. For further structural strength, the backing is textured and irregular, such that heat bonding of the backing with the pad provides further structural strength. Provision for the perforations through the silicone rubber conductive layer also promotes superior electrical characteristics, in that bubbles which may form at the interface during the production process are permitted to migrate to and dissipate at the perforations, rather than being entrapped either at the interface or somewhere within the gel pad.

DESCRIPTION OF THE DRAWINGS

FIG. 1 shows a top isometric view of a preferred embodiment of the principles of the present invention;

FIG. 2 shows a lateral isometric view of the embodiment of FIG. 1;

FIG. 3 shows a transverse isometric view of the embodiment of FIG. 1; and

FIG. 4 shows a partial lateral cutaway of the embodiment of FIG. 1.

BEST MODE FOR CARRYING OUT THE INVENTION

Referring collectively to the drawings, there is shown a preferred embodiment of the principles of the present invention. An electrode is there defined wherein a backing 101 is suitably bonded to a conductive pad 102. Integral with the backing layer 101 is a raised protuberance 103, further defining therein a slot 104 for receipt of an electrical lead or connection from external stimulating or the like apparatus (not shown). A multiplicity of perforations 105, preferably in the form of a rectangular grid pattern, are provided over the surface of the backing layer 101, with each perforation 105 extending completely through the backing layer 101.

In a preferred embodiment, the backing layer 101 and its integral external connection protuberance 103 is composed of conductive silicone rubber having a minimum tensile strength of 650 lbs. per square inch, and a maximum volume resistivity of 10 ohm-cm. Such materials are readily commercially available.

In a preferred embodiment, the electrically conductive flexible pad, which is to be adhesive to the skin of the patient, is composed of polymer adhesive gels such as set forth in U.S. Pat. No. 4,066,0788 to Berg, or alternatively of karaya gum material. Karaya gums are commercially available in bulk (commonly used as seal materials for colostomy patients), and the impedance of the material may be readily adjusted to the desired current capacity of the electrode by simple melting and addition of saline solution to the karaya melt. Pads of proper thickness and electrical conductivity characteristics may thereby be formed. In a preferred embodiment, the perforations 105 are spaced approximately 38 millimeters apart, and are 1.59 millimeters in diameter. It will be appreciated, of course, that in accordance with the knowledge of those of ordinary skill in the art, the spacing and the size of the perforations 105 may be altered in order to yield appropriate current density and distribution characteristics for the overall electrode.

In a preferred embodiment, the electrode is formed by providing not only perforations 105 in the backing layer 101, but furthermore by providing an irregular texture to the lower surface of the backing 101, that is to the interface between pad 102 and backing 101. Thereupon, the pad 102 is applied to the backing 101 by a heat melting process and/or dissolved by aqueous solution. During the course of the application of the melt to the backing 101, the gel rises into the perforations 105 in meniscus fashion (refer to FIG. 4) and there sets. This structure, in combination with the texture upon the bottom of the backing 101, provides an excellent overall structure from the standpoint of capacity to withstand tensile and shear forces upon removal of the electrode from the patient, or movement and adjustment of the electrode upon the patient. Should bubbles be formed in the melt during the fabrication process, their tendency will be to dissipate in the openings 105, thereby promoting uniformity of electrical characteristics of the electrode.

Since the backing 101 and 103 is composed of an integral structure of conductive silicone rubber, external apparatus may be coupled to the electrode by the simple expediency of insertion of a suitable plug into the slot 104. A slot of rectangular cross-section is incorporated into the embodiment of the drawings, and it will be apparent that the 104 cross-section may be specified to mate with a given type of connector or plus from a stimulator. The cross-sectional shape of protuberance 103 may correspondingly be altered. The foregoing has set forth preferred embodiments of the principles of the present invention, but it will be apparent that numerous alternative embodiments will occur to those of ordinary skill in the art without departure from the spirit or scope of the principles of the present invention.

I claim:

1. The method of constructing a transcutaneous electrical nerve stimulation electrode for delivering electrical energy to a patient comprising:

perforating an electrically conductive silicone rubber backing layer with a grid of regularly spaced apertures completely therethrough;

melting a quantity of electrically conductive adhesive material;

applying said melted quantity of adhesive material to one surface of said backing layer and permitting said melted quantity of adhesive to flow at least partially into the interior of said perforations in said backing layer;

cooling said melted quantity of adhesive material to form an adhesive pad on said surface of said layer to form a corresponding plurality of projections on said adhesive pad extending into said plurality of perforations in said backing layer so as to form a tight mechanical contact with at least a part of the inner surface of said perforations to increase the mechanical and adhesive bond between said backing layer and said adhesive pad;

during the application of said melted quantity of adhesive material to said surface of said backing layer, eliminating bubbles whcih may form at the interface between said adhesive pad and said backing layer through said perforations in said backing layer.

2. The method of claim 1 wherein the melted quantity of adhesive material is replaced by an aqueous solution of adhesive material which is coated on said one surface of said backing layer and allowed to dry.

* * * * *